US007922096B2

(12) United States Patent
Eilersen

(10) Patent No.: US 7,922,096 B2
(45) Date of Patent: Apr. 12, 2011

(54) SUPPORT FOR A CARTRIDGE FOR TRANSFERRING AN ELECTRONICALLY READABLE ITEM OF INFORMATION FROM THE CARTRIDGE TO AN ELECTRONIC CIRCUIT

(75) Inventor: Michael Eilersen, Hvidovre (DK)

(73) Assignee: Novo Nordisk A/S, Bagsvaerd (DK)

( * ) Notice: Subject to any disclaimer, the term of this patent is extended or adjusted under 35 U.S.C. 154(b) by 9 days.

(21) Appl. No.: 12/568,153

(22) Filed: Sep. 28, 2009

(65) Prior Publication Data

US 2010/0012735 A1    Jan. 21, 2010

Related U.S. Application Data

(63) Continuation of application No. 11/296,991, filed on Dec. 8, 2005, now Pat. No. 7,621,456, which is a continuation of application No. 09/925,792, filed on Aug. 9, 2001, now Pat. No. 6,994,261.

(60) Provisional application No. 60/229,106, filed on Aug. 30, 2000.

(30) Foreign Application Priority Data

Aug. 10, 2000    (DK) .................................. 2000 01200

(51) Int. Cl.
    *G06K 19/06*    (2006.01)
(52) U.S. Cl. .................. 235/492; 235/454; 235/375
(58) Field of Classification Search .................. 235/492, 235/454, 375, 487
    See application file for complete search history.

(56) References Cited

U.S. PATENT DOCUMENTS 3,700,862 A    10/1972    Snook et al.
3,809,863 A    5/1974    Oberg
3,916,157 A    10/1975    Roulette et al.
(Continued)

FOREIGN PATENT DOCUMENTS

CN    248165    12/1987
(Continued)

OTHER PUBLICATIONS

Office Action dated Jan. 4, 2008 from U.S. Appl. No. 11/396,889, an application filed Apr. 3, 2006 by Christoffersen et al.

(Continued)

*Primary Examiner* — Ahshik Kim
(74) *Attorney, Agent, or Firm* — Wesley A. Nicolas

(57) ABSTRACT

The invention relates to: A support (15) for a cartridge (10) provided with one or more electronically readable information carrying areas (121, 122, 123, 124, 125, 126, 127). The invention further relates to the use of a composite material for a support. The object of the present invention is to provide means, which are capable of securely transferring information with an increased density from a cartridge to an electronic circuit, and which are flexible and may be customized to a variety of physical designs. The problem is solved in that the support (15) for the cartridge (10) is at least partially constituted by one or more electrically connecting supports (151), each comprising a number of closely spaced mutually electrically insulated conductors (1511) embedded in an electrically insulating material (1512, 155) that stretches from one of the supporting surfaces of the cartridge to a contact area (163) for receiving and transferring the information, when said cartridge (10) is positioned in said support (15). This has the advantage of providing a flexible solution, allowing a large information density on a cartridge to be safely transferred to an electronic circuit. The invention may be used e.g. in connection with replaceable medication cartridges for medication delivery devices and with other cartridges from which an item of information is to be electronically transferred.

2 Claims, 10 Drawing Sheets

U.S. PATENT DOCUMENTS

| | | | |
|---|---|---|---|
| 3,998,513 A | 12/1976 | Kobayashi et al. |
| 4,179,212 A | 12/1979 | Lahr |
| 4,327,283 A | 4/1982 | Heyman et al. |
| 4,355,300 A | 10/1982 | Weber |
| 4,420,754 A | 12/1983 | Andermo |
| 4,449,042 A | 5/1984 | Hampson et al. |
| 4,476,149 A | 10/1984 | Poppe et al. |
| 4,476,381 A | 10/1984 | Rubin |
| 4,591,707 A | 5/1986 | Stenzel et al. |
| 4,625,101 A | 11/1986 | Hinks et al. |
| 4,636,786 A | 1/1987 | Haertling |
| 4,693,574 A | 9/1987 | Ohnuki et al. |
| 4,731,526 A | 3/1988 | Knoll et al. |
| 4,739,377 A | 4/1988 | Allen |
| 4,810,867 A | 3/1989 | Speicher |
| 4,850,966 A | 7/1989 | Grau et al. |
| 4,853,521 A | 8/1989 | Claeys et al. |
| 4,857,716 A | 8/1989 | Gombrich et al. |
| 4,880,014 A | 11/1989 | Zarowitz et al. |
| 4,896,946 A | 1/1990 | Suzuki et al. |
| 4,930,263 A | 6/1990 | Rando |
| 4,950,246 A | 8/1990 | Muller |
| 4,959,056 A | 9/1990 | Dombrowski et al. |
| 4,978,335 A | 12/1990 | Arthur |
| 5,059,776 A | 10/1991 | Antes |
| 5,077,635 A | 12/1991 | Bollhagen et al. |
| 5,078,683 A | 1/1992 | Sancoff et al. |
| 5,091,798 A | 2/1992 | Hibino |
| 5,132,026 A | 7/1992 | Baluyet et al. |
| 5,153,827 A | 10/1992 | Courte et al. |
| 5,174,766 A | 12/1992 | Yoshizawa et al. |
| 5,176,502 A | 1/1993 | Sanderson et al. |
| 5,196,683 A | 3/1993 | Marom et al. |
| 5,305,147 A | 4/1994 | Hasegawa et al. |
| 5,311,364 A | 5/1994 | Kanoshima et al. |
| 5,317,506 A | 5/1994 | Coutre et al. |
| 5,336,871 A | 8/1994 | Colgate, Jr. |
| 5,379,131 A | 1/1995 | Yamazaki |
| 5,394,206 A | 2/1995 | Cocca |
| 5,403,616 A | 4/1995 | Hattori et al. |
| 5,418,649 A | 5/1995 | Igarashi |
| 5,422,472 A | 6/1995 | Tavislan et al. |
| 5,430,278 A | 7/1995 | Krieg et al. |
| 5,432,329 A | 7/1995 | O'Boyle et al. |
| 5,461,239 A | 10/1995 | Atherton |
| 5,523,560 A | 6/1996 | Manique et al. |
| 5,569,212 A | 10/1996 | Brown |
| 5,585,615 A | 12/1996 | Iwanami et al. |
| 5,593,390 A | 1/1997 | Castellano et al. |
| 5,628,309 A | 5/1997 | Brown |
| 5,637,854 A | 6/1997 | Thomas |
| 5,643,212 A | 7/1997 | Coutre et al. |
| 5,675,380 A | 10/1997 | Florent |
| 5,686,725 A | 11/1997 | Maruyama et al. |
| 5,747,350 A | 5/1998 | Sattler |
| 5,757,521 A | 5/1998 | Walters et al. |
| 5,764,457 A | 6/1998 | Uhde et al. |
| 5,777,303 A | 7/1998 | Berney |
| 5,782,814 A | 7/1998 | Brown et al. |
| 5,786,584 A | 7/1998 | Button et al. |
| 5,792,117 A | 8/1998 | Brown |
| 5,793,502 A | 8/1998 | Bianco |
| 5,821,521 A | 10/1998 | Bridgelall et al. |
| 5,821,524 A | 10/1998 | Horlbeck |
| 5,880,683 A | 3/1999 | Brandestini |
| 5,882,463 A | 3/1999 | Tompkin et al. |
| 5,895,369 A | 4/1999 | Flower |
| 5,902,990 A | 5/1999 | Stewart |
| 5,925,867 A | 7/1999 | Hagimoto |
| 5,954,700 A | 9/1999 | Kovelman |
| 5,986,585 A | 11/1999 | Pusch |
| 6,003,775 A | 12/1999 | Ackley |
| 6,019,745 A | 2/2000 | Gray |
| 6,047,892 A | 4/2000 | Schuessler et al. |
| 6,053,415 A | 4/2000 | Norwood |
| 6,068,615 A | 5/2000 | Brown et al. |
| 6,090,064 A | 7/2000 | Reilly et al. |
| 6,110,148 A | 8/2000 | Brown et al. |
| 6,110,152 A | 8/2000 | Kovelman |
| 6,168,080 B1 | 1/2001 | Verschuur et al. |
| 6,177,683 B1 | 1/2001 | Kolesar et al. |
| 6,202,929 B1 | 3/2001 | Verschuur et al. |
| 6,215,508 B1 | 4/2001 | Bryan et al. |
| 6,265,466 B1 | 7/2001 | Glatkowski et al. |
| 6,274,092 B1 | 8/2001 | Itoh |
| 6,329,813 B1 | 12/2001 | Andermo |
| 6,352,523 B1 | 3/2002 | Brown et al. |
| 6,372,293 B1 | 4/2002 | Mathus et al. |
| 6,435,175 B1 | 8/2002 | Stenzler |
| 6,475,192 B1 | 11/2002 | Reilly et al. |
| 6,533,183 B2 | 3/2003 | Aasmul et al. |
| 6,598,796 B2 | 7/2003 | Harrop |
| 6,652,812 B1 | 11/2003 | Vartianen et al. |
| 6,669,090 B2 | 12/2003 | Eilersen |
| 6,700,391 B2 | 3/2004 | Strack et al. |
| 6,813,868 B2 | 11/2004 | Baldwin et al. |
| 6,854,653 B2 | 2/2005 | Eilersen |
| 6,954,700 B2 | 10/2005 | Higashida et al. |
| 6,957,522 B2 | 10/2005 | Baldwin et al. |
| 6,976,349 B2 | 12/2005 | Baldwin et al. |
| 6,994,261 B2 | 2/2006 | Eilersen |
| 7,018,363 B2 | 3/2006 | Cowan et al. |
| 7,041,941 B2 | 5/2006 | Faries et al. |
| 7,061,831 B2 | 6/2006 | De La Huerga |
| 7,077,332 B2 | 7/2006 | Verschuur et al. |
| 7,104,973 B2 | 9/2006 | Woolston et al. |
| 7,108,184 B2 | 9/2006 | Mase et al. |
| 2001/0001472 A1 | 5/2001 | Sano et al. |
| 2001/0013544 A1 | 8/2001 | Rathus et al. |
| 2001/0015202 A1 | 8/2001 | Miller |
| 2001/0034506 A1 | 10/2001 | Hirschman et al. |
| 2002/0000471 A1 | 1/2002 | Aasmul et al. |
| 2002/0012176 A1 | 1/2002 | Ning |
| 2002/0020654 A1 | 2/2002 | Eilersen |
| 2002/0022821 A1 | 2/2002 | Eilersen |
| 2002/0063156 A1 | 5/2002 | Marchand |
| 2002/0106309 A1 | 8/2002 | Mathus et al. |
| 2002/0117549 A1 | 8/2002 | Lee |
| 2002/0117579 A1 | 8/2002 | Kotoulas et al. |
| 2002/0123078 A1 | 9/2002 | Seul et al. |
| 2003/0015590 A1 | 1/2003 | Chen |
| 2003/0039590 A1 | 2/2003 | Lodge |
| 2003/0116630 A1 | 6/2003 | Carey et al. |
| 2003/0143614 A1 | 7/2003 | Drmanac |
| 2003/0205625 A1 | 11/2003 | Eilersen |
| 2003/0233069 A1 | 12/2003 | Gillespie et al. |
| 2004/0008853 A1 | 1/2004 | Pelrine et al. |
| 2004/0024368 A1 | 2/2004 | Broselow |
| 2004/0046032 A1 | 3/2004 | Urano et al. |
| 2004/0051368 A1 | 3/2004 | Caputo et al. |
| 2004/0141426 A1 | 7/2004 | Kawasaki et al. |
| 2004/0155113 A1 | 8/2004 | Urano et al. |
| 2004/0178255 A1 | 9/2004 | Eich et al. |
| 2004/0200558 A1 | 10/2004 | Stevens et al. |
| 2004/0207385 A1 | 10/2004 | Gafner et al. |
| 2004/0210199 A1 | 10/2004 | Atterbury et al. |
| 2005/0006472 A1 | 1/2005 | Verschuur et al. |
| 2005/0035207 A1 | 2/2005 | Philyaw et al. |
| 2005/0060059 A1 | 3/2005 | Klein et al. |
| 2005/0116033 A1 | 6/2005 | Moore |
| 2005/0156318 A1 | 7/2005 | Douglas |
| 2005/0182360 A1 | 8/2005 | Yeandel et al. |
| 2005/0236603 A1 | 10/2005 | Faris |
| 2005/0283116 A1 | 12/2005 | Eakins et al. |
| 2006/0097877 A1 | 5/2006 | Baba et al. |
| 2006/0118612 A1 | 6/2006 | Christoffersen et al. |
| 2006/0125491 A1 | 6/2006 | Grishin et al. |
| 2006/0129104 A1 | 6/2006 | Cowan et al. |
| 2006/0138233 A1 | 6/2006 | Kemppainen et al. |
| 2006/0164002 A1 | 7/2006 | O'Brien et al. |
| 2006/0170981 A1 | 8/2006 | Ricks et al. |
| 2006/0176267 A1 | 8/2006 | Honeyman et al. |
| 2006/0226238 A1 | 10/2006 | Salib et al. |
| 2006/0243804 A1 | 11/2006 | Christoffersen et al. |
| 2007/0080234 A1 | 4/2007 | Demoy |
| 2008/0015510 A1 | 1/2008 | Sandoz et al. |
| 2009/0088701 A1 | 4/2009 | Larsen |

FOREIGN PATENT DOCUMENTS

| | | |
|---|---|---|
| CN | 1013704 | 8/1991 |
| CN | 1051152 | 9/1993 |
| DE | 2636634 | 2/1978 |
| DE | 3712089 | 10/1988 |
| DE | 4234016 | 4/1993 |
| DE | 4402319 | 8/1994 |
| DE | 19504111 | 8/1995 |
| DE | 19637967 | 10/1997 |
| DE | 19814687 | 2/1999 |
| DE | 10035192 | 10/2001 |
| EP | 0235691 | 2/1987 |
| EP | 398717 | 11/1990 |
| EP | 402553 | 12/1990 |
| EP | 0364010 | 4/1993 |
| EP | 626660 | 11/1994 |
| EP | 685810 | 12/1994 |
| EP | 0690457 | 5/1995 |
| EP | 0336778 | 12/1995 |
| EP | 716290 | 6/1996 |
| EP | 0492954 | 10/1996 |
| EP | 833273 | 4/1998 |
| EP | 0833278 | 4/1998 |
| EP | 0573129 | 8/1998 |
| EP | 0911859 | 10/1998 |
| EP | 0588427 | 11/1998 |
| EP | 1142643 | 10/2001 |
| EP | 1143643 | 10/2001 |
| EP | 1246127 | 3/2002 |
| EP | 1193641 | 4/2002 |
| EP | 1503185 | 2/2005 |
| FR | 2771111 | 5/1999 |
| GB | 2088163 | 6/1982 |
| GB | 2159007 | 11/1985 |
| GB | 2216259 | 10/1989 |
| GB | 2287551 | 9/1995 |
| GB | 2309801 | 8/1997 |
| GB | 2336927 | 11/1999 |
| GB | 2341965 | 3/2000 |
| JP | 56-094475 | 7/1981 |
| JP | 59131917 | 7/1984 |
| JP | 60163027 | 8/1985 |
| JP | 63-100303 A | 5/1988 |
| JP | 2-85370 A | 3/1990 |
| JP | 2-188702 | 7/1990 |
| JP | 2-250083 | 10/1990 |
| JP | 3-27037 A | 2/1991 |
| JP | 4-222084 A | 8/1992 |
| JP | 4-233680 A | 8/1992 |
| JP | 4-233684 A | 8/1992 |
| JP | 5006449 | 1/1993 |
| JP | 5-500917 | 2/1993 |
| JP | 05-314296 | 11/1993 |
| JP | 06-171194 | 6/1994 |
| JP | 6-333102 | 12/1994 |
| JP | 7-098752 | 4/1995 |
| JP | 07-271890 | 10/1995 |
| JP | 8-106648 | 4/1996 |
| JP | 8-118864 | 5/1996 |
| JP | 8-179475 | 7/1996 |
| JP | 8-220994 | 8/1996 |
| JP | 8-262980 | 10/1996 |
| JP | 9-16703 | 1/1997 |
| JP | 9-034361 | 2/1997 |
| JP | 9-091364 | 4/1997 |
| JP | 9-192220 | 7/1997 |
| JP | 09-223181 | 8/1997 |
| JP | 09-274637 | 10/1997 |
| JP | 11135172 | 10/1997 |
| JP | 11162591 | 11/1997 |
| JP | 10-105635 | 4/1998 |
| JP | 10-268777 | 10/1998 |
| JP | 11-180079 | 7/1999 |
| JP | 11-276583 | 10/1999 |
| JP | 11-316877 | 11/1999 |
| JP | 2000-040119 | 2/2000 |
| JP | 2000-272191 | 3/2000 |
| JP | 2001-043301 | 2/2001 |
| JP | 2001-075480 | 3/2001 |
| JP | 2002-082120 | 3/2002 |
| JP | 2002-517737 | 6/2002 |
| JP | 4-233624 B2 | 12/2008 |
| WO | WO 91/04759 | 4/1991 |
| WO | WO 92/17231 | 10/1992 |
| WO | WO 93/12828 | 7/1993 |
| WO | WO 94/08647 | 4/1994 |
| WO | WO 94/12235 | 6/1994 |
| WO | WO 95/24317 | 9/1995 |
| WO | WO 95/28190 | 10/1995 |
| WO | WO 9960533 | 11/1999 |
| WO | WO 9965548 | 12/1999 |
| WO | WO 00/42678 | 7/2000 |
| WO | WO 01/22348 | 3/2001 |
| WO | WO 01/54055 | 7/2001 |
| WO | WO 01/62322 | 8/2001 |
| WO | WO 01/70304 | 9/2001 |
| WO | WO 01/84542 | 11/2001 |
| WO | WO 02/11792 | 2/2002 |
| WO | WO 02/13133 | 2/2002 |
| WO | WO 02/092153 | 11/2002 |
| WO | WO 02/095675 | 11/2002 |
| WO | WO 03/017915 | 3/2003 |
| WO | WO 03/020598 | 3/2003 |
| WO | WO 03/038738 | 5/2003 |
| WO | WO 2004/084795 | 10/2004 |
| WO | WO 2004/097715 | 11/2004 |
| WO | WO 2005/075010 | 8/2005 |
| WO | WO 2005/089835 | 9/2005 |
| WO | WO 2007/039148 | 4/2007 |
| WO | WO 2007/107562 | 9/2007 |
| WO | WO 2007/116090 | 10/2007 |
| WO | WO 2007/122253 | 11/2007 |
| WO | WO 2009/015933 | 2/2009 |

OTHER PUBLICATIONS

International Search Report for PCT/EP07/054069, mailed Sep. 17, 2007.
International Search Report for PCT/EP07/053558, mailed Jul. 23, 2007.
International Search Report for PCT/EP06/009240, mailed Jan. 4, 2007.
CN 1051152 English Abstract, Sep. 15, 1993.
CN 1013704 English Abstract, Aug. 28, 1991.
DE 19814687 Machine Translation, Feb. 18, 1999.
DE 19637967 English Abstract, Oct. 30, 1997.
DE 19504111 Machine Translation, Aug. 15, 1995.
DE 10035192 Machine Translation, Oct. 11, 2001.
DE 4402319 English Abstract, published Aug. 4, 1994.
DE 4234016 English Abstract, Apr. 15, 1993.
DE 2636634 English Abstract, Feb. 16, 1978.
FR 2771111 Machine Translation, May 21, 1999.
JP 2002-517737 Machine Translation, Jun. 18, 2002.
JP 2000-040119 Machine Translation, Feb. 8, 2000.
JP 11-180079 Machine Translation, Jul. 6, 1999.
JP 11-162591 Machine Translation, Jun. 18, 1999.
JP 11-135172 Machine Translation, May 21, 1999.
JP 10-268777 Machine Translation, Oct. 9, 1998.
JP 10-105635 Machine Translation, Apr. 24, 1998.
JP 9-192220 Machine Translation, Jul. 29, 1997.
JP 9-091364 Machine Translation, Apr. 4, 1997.
JP 9-034361 Machine Translation, Feb. 7, 1997.
JP 9-16703 Machine Translation, Jan. 17, 1997.
JP 8-262980 Machine Translation, Oct. 11, 1996.
JP 8-220994 Machine Translation, Aug. 30, 1996.
JP 8-179475 Machine Translation, Jul. 12, 1996.
JP 8-118864 Machine Translation, May 14, 1996.
JP 8-106648 Machine Translation, Apr. 23, 1996.
JP 7-098752 Machine Translation, Apr. 11, 1995.
JP 6-333102 Machine Translation, Dec. 2, 1994.
JP 63-100303A English Abstract, May 2, 1988.
JP 6-163027 Machine Translation, Jun. 10, 1994.
JP 59-131917 English Abstract, Jul. 28, 1984.
JP 5-500917 English Abstract, Feb. 25, 1993.
JP 4-233684A English Abstract, Aug. 21, 1992.

JP 4-233680A English Abstract, Aug. 21, 1992.
JP 4-233624B2 Machine Translation, Dec. 19, 2008.
JP 4-222084 English Abstract, Aug. 12, 1992.
JP 3-27037A English Abstract, Feb. 5, 1991.
JP 2-250083 English Abstract, Oct. 5, 1990.
JP 2-188702 English Abstract, Jul. 24, 1990.
JP 2-85370 English Abstract, Mar. 26, 1990.
Notice of Allowance mailed Sep. 17, 2009 in U.S. Appl. No. 11/296,991 filed Dec. 8, 2005 by Eilersen et al.
Notice of Allowance mailed Apr. 30, 2009 in U.S. Appl. No. 11/296,991 filed Dec. 8, 2005 by Eilersen et al.
Non-Final Office Action mailed Oct. 14, 2008 in U.S. Appl. No. 11/296,991 filed Dec. 8, 2005 by Eilersen et al.
Corrected Notice of Allowance mailed Jun. 19, 2009 in U.S. Appl. No. 11/232,469 filed Sep. 19, 2005 by Christoffersen et al.
Notice of Allowance mailed Jun. 8, 2009 in U.S. Appl. No. 11/232,469 filed Sep. 19, 2005 by Christoffersen et al.
Non-Final Office Action mailed Dec. 17, 2008 in U.S. Appl. No. 11/232,469 filed Sep. 19, 2005 by Christoffersen et al.
Final Office Action mailed Jul. 2, 2008 in U.S. Appl. No. 11/232,469 filed Sep. 19, 2005 by Christoffersen et al.
Non-Final Office Action mailed Jan. 3, 2008 in U.S. Appl. No. 11/232,469 filed Sep. 19, 2005 by Christoffersen et al.
Non-Final Office Action mailed Jun. 19, 2007 in U.S. Appl. No. 11/232,469 filed Sep. 19, 2005 by Christoffersen et al.
Non-Final Office Action mailed Oct. 23, 2003 in U.S. Appl. No. 10/463,915 filed Jun. 18, 2003 by Eilersen et al.
Non-Final Office Action mailed Apr. 15, 2004 in U.S. Appl. No. 10/463,915 filed Jun. 18, 2003 by Eilersen et al.
Notice of Allowance mailed Aug. 16, 2004 in U.S. Appl. No. 10/463,915 filed Jun. 18, 2003 by Eilersen et al.
Notice of Allowance mailed Aug. 13, 2003 in U.S. Appl. No. 09/925,995, filed Aug. 9, 2001 by Eilersen et al.
Non-Final Office Action mailed Nov. 12, 2002 in U.S. Appl. No. 09/925,995, filed Aug. 9, 2001 by Eilersen et al.
Notice of Allowance mailed Aug. 11, 2005 in U.S. Appl. No. 09/925,792, filed Aug. 9, 2001 by Eilersen et al.
Non-Final Office Action mailed Apr. 4, 2005 in U.S. Appl. No. 09/925,792, filed Aug. 9, 2001 by Eilersen et al.
Notice of Allowance mailed Oct. 8, 2002 in U.S. Appl. No. 09/846,799 filed May 1, 2001 by Aasmul et al.
Non-Final Office Action mailed May 8, 2002 in U.S. Appl. No. 09/846,799 filed May 1, 2001 by Aasmul et al.
English Abstract of JP56-094475 Published Jul. 30, 1981.
English Abstract of JP5006449 Published Jan. 14, 1993.
English Abstract of JP06-171194 Published Jun. 21, 1994.
English Abstract of JP11-276583 Published Oct. 12, 1999.
Translation on Japanese Office Action in Japanese Application No. 2002-518416 filed Feb. 10, 2003.

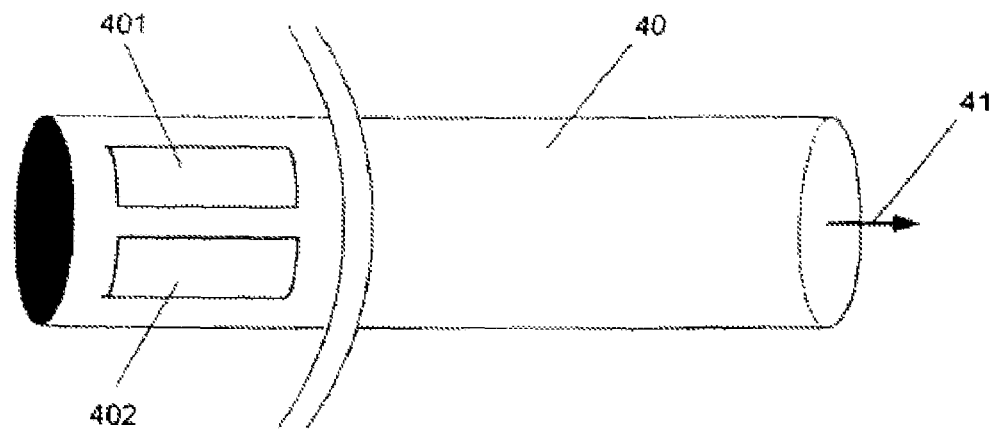
Fig. 4.a
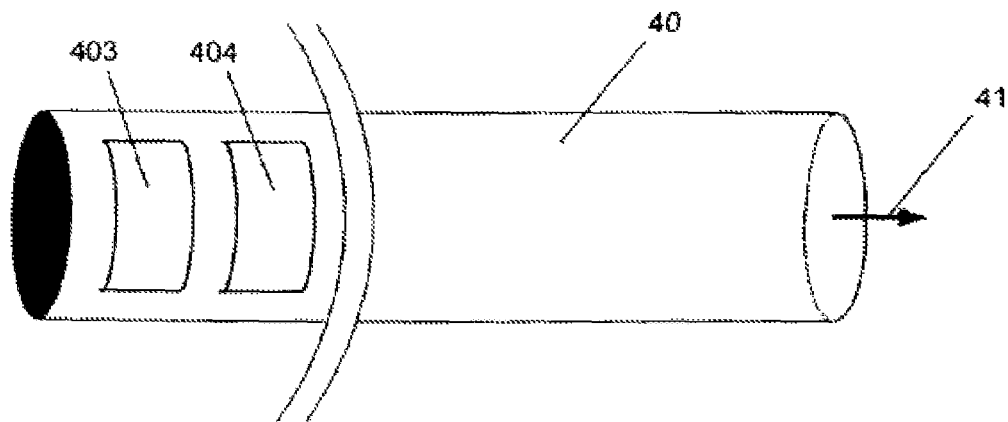
Fig. 4.b
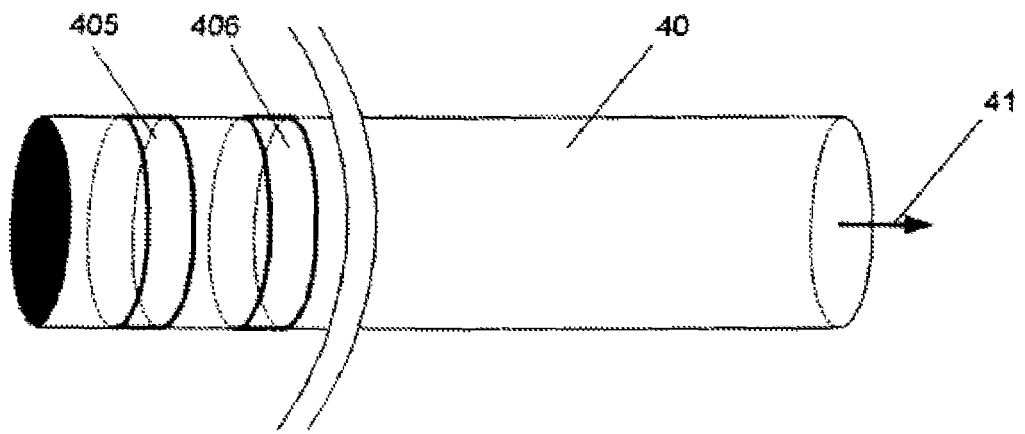
Fig. 4.c

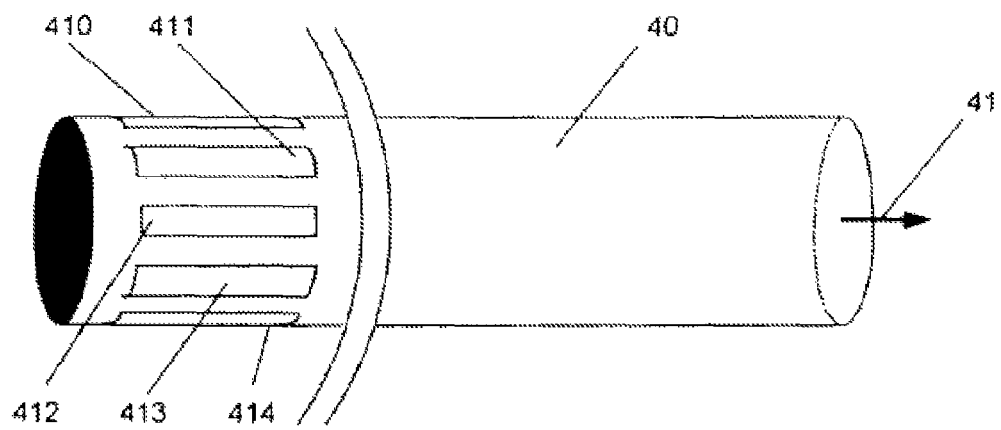
Fig. 4.d
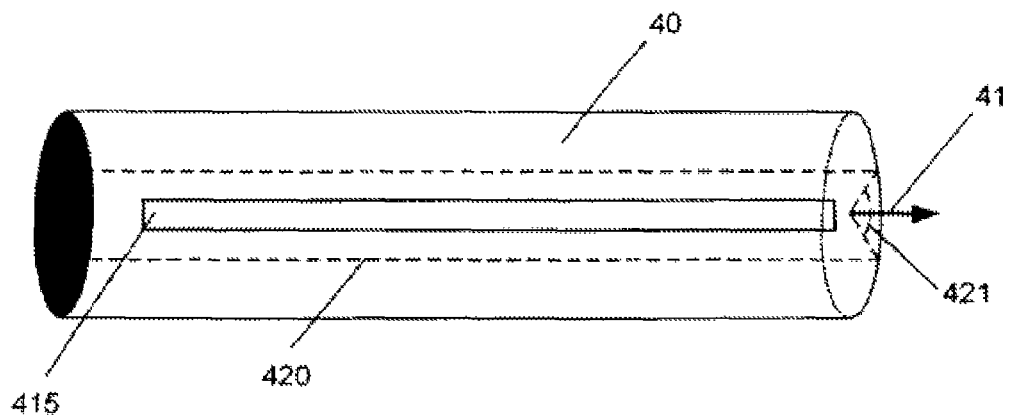
Fig. 4.e

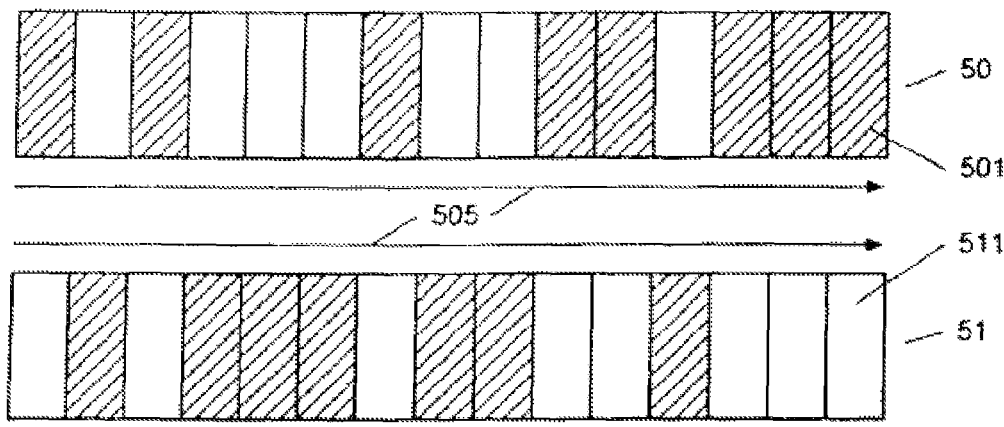
Fig. 5.a
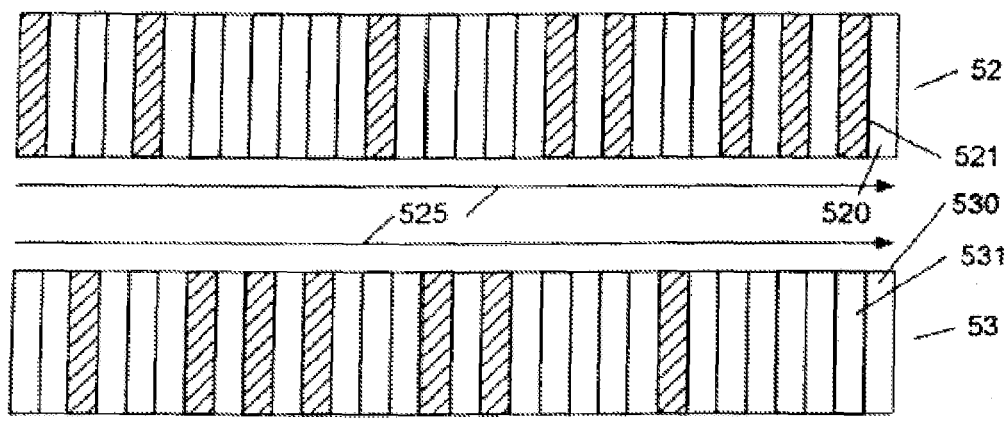
Fig. 5.b

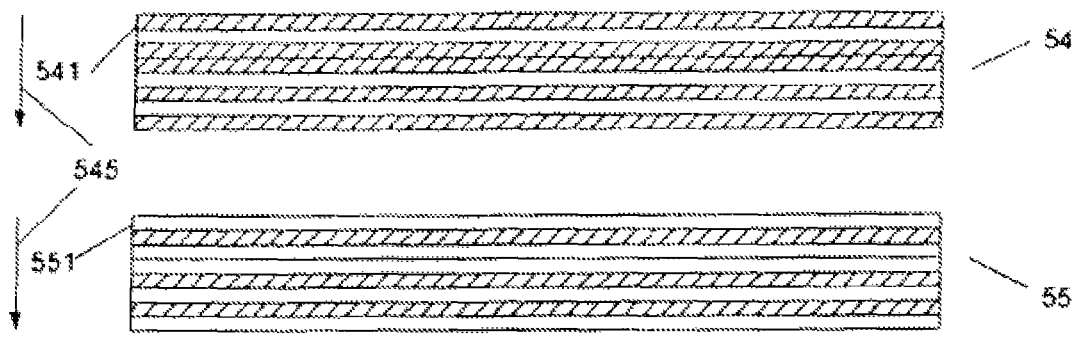
Fig. 5.c
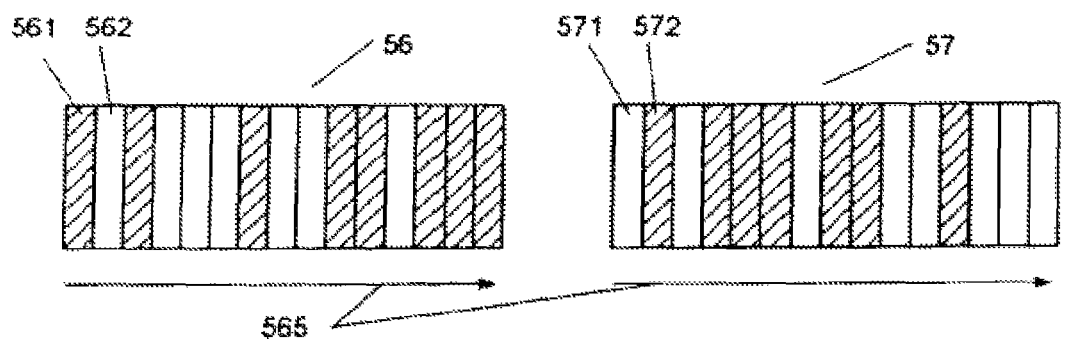
Fig. 5.d
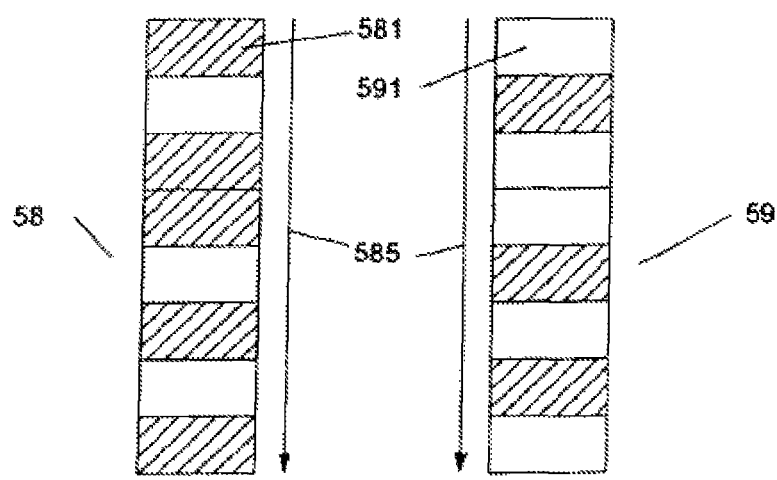
Fig. 5.e

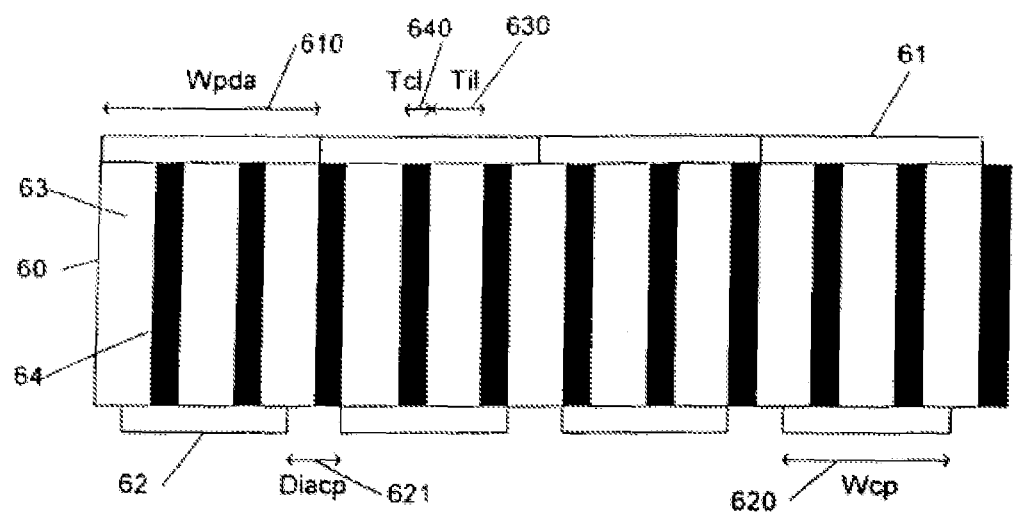
Fig. 6.a
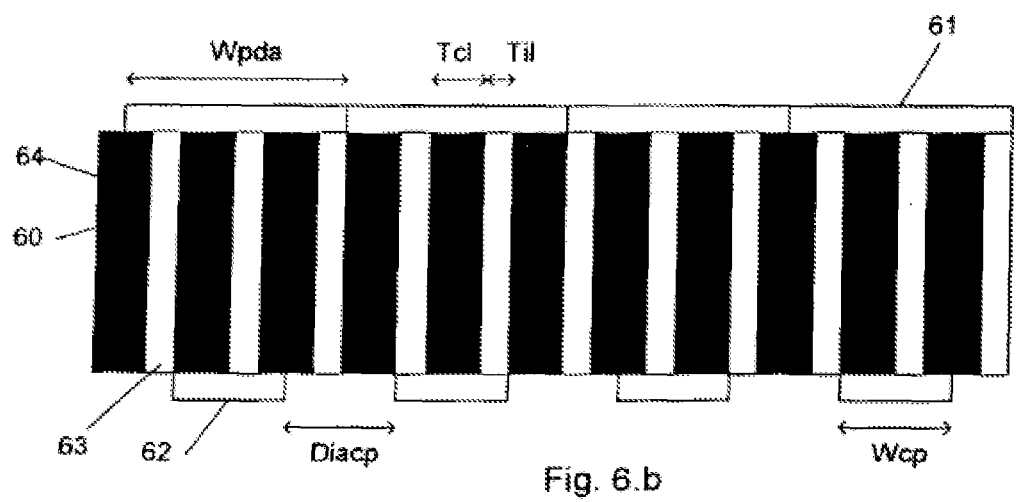
Fig. 6.b
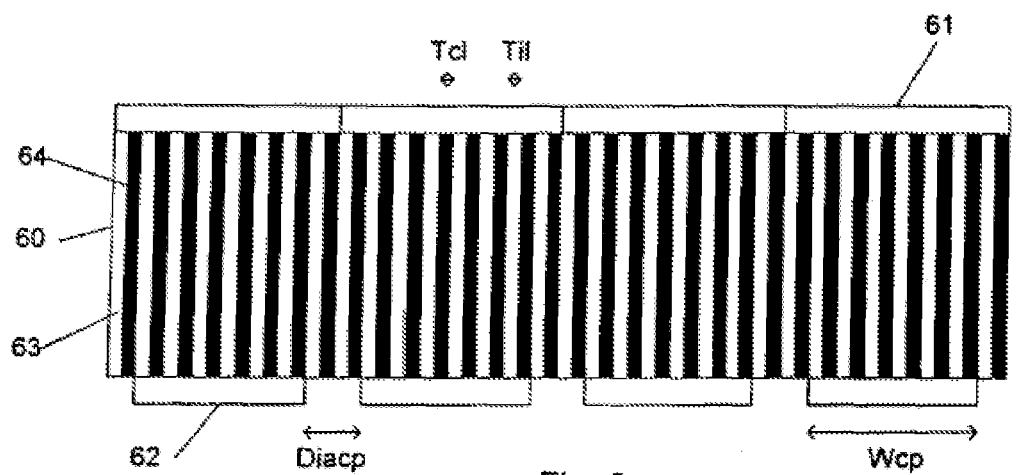
Fig. 6.c

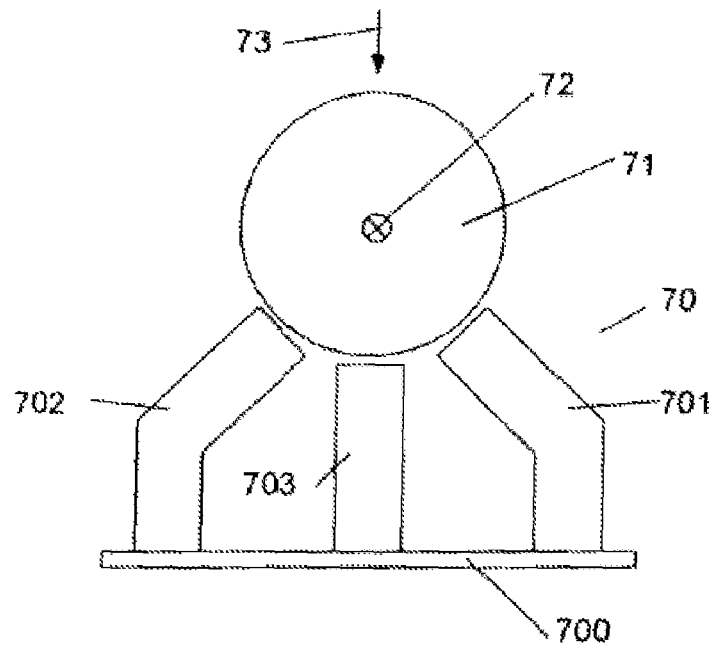
Fig. 7.a
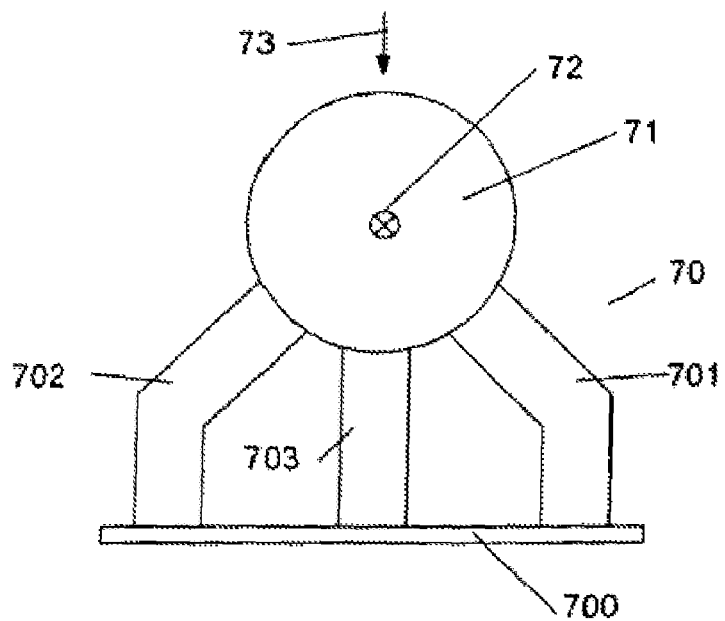
Fig. 7.b

SUPPORT FOR A CARTRIDGE FOR TRANSFERRING AN ELECTRONICALLY READABLE ITEM OF INFORMATION FROM THE CARTRIDGE TO AN ELECTRONIC CIRCUIT

CROSS-REFERENCE TO RELATED PATENT APPLICATIONS

This patent application is a continuation of copending U.S. patent application Ser. No. 11/296,991 filed Dec. 8, 2005, which is a continuation of U.S. patent application Ser. No. 09/925,792 filed on Aug. 9, 2001 (U.S. Pat. No. 6,994,261), and claims priority of Danish Patent Application PA 2000 01200 filed on Aug. 10, 2000 and priority of U.S. Patent Application 60/229,106 filed on Aug. 30, 2000, and the contents of all of which are hereby incorporated by reference.

TECHNICAL FIELD OF THE INVENTION

The invention relates to the electronic marking of cartridges or the like.

The invention relates specifically to: A support for a cartridge provided with one or more electronically readable information carrying areas.

The invention furthermore relates to: The use of a composite material, comprising a number of closely spaced mutually electrically insulated conductors embedded in an electrically insulating material.

DESCRIPTION OF RELATED ART

The following account of the prior art relates to one of the areas of application of the present invention, the electronic marking of medication cartridges.

The marking of medication cartridges to be able to electronically read details of its contents is of increasing importance, i.a. to ensure a safe and convenient use of the medication in connection with a patient's self-treatment of a disease such as diabetes. In order for the user to feel secure about handling the medication it is important that errors in his or hers use of the drug are avoided.

One remedy to avoid errors is an intelligent marking of the contents (i.e. drug, concentration, relevant dose, last day of use, etc.) of the medication cartridge. This includes a visually intelligible marking of the cartridge for reading by a user as well as an electronically readable code for use by a processing unit of the medication delivery device, the processing unit being used for monitoring and controlling the actual delivery of the medication to the user and for making a record of the drug administration history, etc. In other words a certain area of the medication cartridge must be reserved to hosting an increasing amount of information.

The information on a medication cartridge must be provided in a safe and simple way that is easily transferred from the cartridge to an electronic processing circuit. U.S. Pat. No. 5,954,700 discloses a cartridge for containing a fluid and for use with an electronic delivery device that includes a cartridge housing for holding the fluid, and an information providing source. The information-providing source may be a set of wires and contacts, or contact bands that provide the predetermined information to an electronic delivery device by producing a binary code. To implement a specific binary code requires an individual customisation of the cartridge as regards the contacts or contact bands and the wires connecting them to a positive or negative voltage. Our co-pending application "Electronic marking of a medication cartridge" discloses a method of marking a medication cartridge that is simple and improves safety in reading. The method provides the information redundantly and implements in one of its embodiments a given binary code by adding insulating areas to a conducting foil (connected to a supply voltage) and transferring the information to a processing unit by means of a support based on the principles outlined in the present patent application.

Another remedy for avoiding errors and for making the user feel comfortable with the handling is that the drug contained in the medication cartridge is visible from outside, so that the user is able to check the color, the uniformity, whether impurities are present, etc. For this reason, as large a part of the surface of the medication cartridge as possible should be free of labels and other opaque items that limit a user's view of the contents. Further, there is a general trend to miniaturization of electronic devices including medication delivery devices, so that they are easy to carry and discreet in use.

DISCLOSURE OF THE INVENTION

Thus there is a need for a way of transferring densely coded information on the, typically curved, surface of a medication cartridge to an electronic circuit connected to a processing circuit, said information being provided in binary form on the cartridge by a mixture of patterns of electrically conducting and electrically insulating wires, areas or patches or the like.

The object of the present invention is to provide means, which are capable of securely transferring information with an increased density from a cartridge to an electronic circuit, and which are flexible and may be customized to a variety of physical designs.

This is achieved according to the invention in that the support for the cartridge is at least partially constituted by one or more electrically connecting supports, each comprising a number of closely spaced mutually electrically insulated conductors embedded in an electrically insulating material that stretches from one of the supporting surfaces of the cartridge to a contact area for receiving and transferring the information, when said cartridge is positioned in said support.

When each of said one or more electrically connecting supports is constituted by alternating layers of electrically conducting material of maximum thickness $T_{cl}$ and electrically insulating material of maximum thickness $T_{il}$, respectively, it is ensured that a simple and flexible solution is provided. By controlling the thicknesses of the two layer types, the maximum density of information may be controlled.

When said support is made of elastic materials, it may be ensured that the support conforms to the shape of the cartridge when the cartridge is positioned in the support with a certain minimum pressure. I.e. it makes the support even more flexible and relaxes the tolerances to its conformity with the cartridge and with the contact area (e.g. pads on a printed circuit board (PCB) for connecting to a processing circuit on the PCB).

In a preferred embodiment said one or more electrically connecting supports are made of elastomeric materials.

In a preferred embodiment said electrically conducting material consists of silicone rubber with a concentration of carbon black sufficient for electrical conduction.

When said cartridge has an axial direction of symmetry, and said information carrying areas are located preferably in one axial end of the cartridge, it is ensured that the main part of the cartridge is not covered by the electronically readable information and may be held free for optical inspection of the contents of the cartridge (in case of a transparent cartridge).

By using a fine layer pitch in the electrically connecting supports, the electronically readable information may be densely written and thus be concentrated to an end of the cartridge that is used for a lid or cover, in which case the whole effective volume available for housing the medication may be open for inspection.

When said cartridge has an axial direction of symmetry, and said information carrying areas are located preferably in an axial direction of the cartridge covering only a limited angular sector, it is ensured that the whole length of the cartridge in its axial direction may be used for coding information and at the same time it is possible to inspect the contents of the cartridge over the full axial length of the cartridge.

In a preferred embodiment said support comprises one electrically connecting support preferably stretching in an axial direction of the cartridge.

When said support comprises two or more electrically connecting supports each stretching preferably in an axial direction of the cartridge and being located side by side along the radial periphery of the cartridge, it is ensured that the electronically readable information may be written several times in information carrying areas distributed along the radial periphery of the cartridge and that two or more of the areas may be simultaneously read. The information in each area may be different, in which case the information capacity is increased. Alternatively, the information in each area may be redundantly provided by coding the same information in all areas or by alternatingly coding its binary true and inverted forms. The redundancy may be used to implement checks to improve reading security.

When the surface of the support facing towards the cartridge, including the one or more electrically connecting supports, in an axial cross section correspond to the surface of the cartridge, it is ensured that the cartridge is received and supported in an optimal way if the support is made of a relatively inelastic material.

When the surface of the support facing towards the cartridge, including the one or more electrically connecting supports, in an axial cross section essentially correspond to the surface of the cartridge, when said cartridge is positioned in said support, it is ensured that the cartridge is received and supported in an optimal way if the support is made of a relatively elastic material.

When said cartridge has an axial direction of symmetry, and said contact area consists of groups of identical and regularly spaced electrically conducting pads of width Wcp in the direction of adjacent pads, adjacent pads being separated by an electrically insulating area of width Diacp, and the following relations between said distances are fulfilled:

$$Diacp > 2*T_{cl}, \text{ and}$$

$$Wcp > T_{il} + T_{cl},$$

it is ensured that the electrical states of adjacent (possibly abutted) predefined positions are not transferred to the same pad ($Diacp > 2*T_{cl}$), and that at least one conducting layer contacts any given pad ($Wcp > T_{il} + T_{cl}$).

When said cartridge has an axial direction of symmetry, and said cartridge is provided with a multitude of rectangular, essentially parallel, identically sized information carrying areas of height Hica in the direction of a circumference of said axis of symmetry, said information carrying areas being spaced with equal mutual distance Dica along the periphery of the cartridge in the direction of a circumference of said axis of symmetry, and said supporting means comprise two rectangular, essentially parallel, identical electrically connecting supports of height Hctm in the direction perpendicular to the axis of symmetry of the cartridge, separated by an electrically insulating volume of width Dctm between the two electrically connecting supports, and the following relations between said distances are fulfilled:

$$Hica < Dctm < 2*Hica + Dica, \text{ and}$$

$$Hctm < Dica < 2*Hctm + Dctm,$$

it is ensured that the cartridge cannot be positioned in such a way that a given information carrying area has contact to two electrically connecting supports at the same time (Hica<Dctm). It is further ensured that the cartridge cannot be positioned in such a way that a given electrically connecting support has contact to two information carrying areas at the same time (Hctm<Dica). It is further ensured that the cartridge cannot be positioned in such a way that the electrically connecting supports fall entirely between two information carrying areas, in which case they would not have contact to any of the information carrying areas of the cartridge (Dica<2*Hctm+Dctm). It is further ensured that the cartridge cannot be positioned in such a way that two adjacent information carrying areas fall entirely between the electrically connecting supports, in which case the latter might not have contact to any of the information carrying areas of the cartridge (Dctm<2*Hica+Dica).

When said information carrying areas of height Hica each consist of electrically conducting and electrically insulating rectangular patches provided at said predefined positions on said cartridge according to a binary representation of said item of information, said patches having a width Wpda abut each other, and the sum of the maximum thicknesses $T_{cl}$ and $T_{il}$ of said alternating layers of electrically conducting and electrically insulating materials, respectively, constituting said electrically connecting supports, is less than the width Wpda of said patches, thus fulfilling the following relation between said distances:

$$Wpda > T_{il} + T_{cl},$$

it is ensured that each patch has contact to at least one of the conducting layers of an electrically connecting support when the cartridge is properly placed in the support.

The use of a composite material, comprising a number of closely spaced mutually electrically insulated conductors embedded in an electrically insulating material is furthermore provided by the present invention. When said composite material is used at least for the partial support of a cartridge and for the transfer of an electronically readable information from information carrying areas on said cartridge to a contact area, a secure transfer of information with an increased density from a cartridge to an electronic circuit is provided.

When said closely spaced mutually electrically insulated conductors embedded in an electrically insulating material are constituted by alternating layers of electrically conducting material and electrically insulating material, respectively, it is ensured that that a simple and flexible solution is provided.

In a preferred embodiment said alternating layers of electrically conducting material and electrically insulating material, respectively are made of elastomeric materials.

BRIEF DESCRIPTION OF THE DRAWINGS

The invention will be explained more fully below in connection with a preferred embodiment and with reference to the drawings in which:

The figures are schematic and simplified for clarity, and they just show details, which are essential to the understanding of the invention, while other details are left out. In general, the reference numerals of a given drawing start with the number of that drawing, i.e. in FIG. 1, reference numerals typically have a 1 as the most significant digit (e.g. 1, 11, 125, 1250). This means on the other hand that functionally identical features occurring in different drawings have different reference numerals.

DETAILED DESCRIPTION OF EMBODIMENTS

Figure 1:
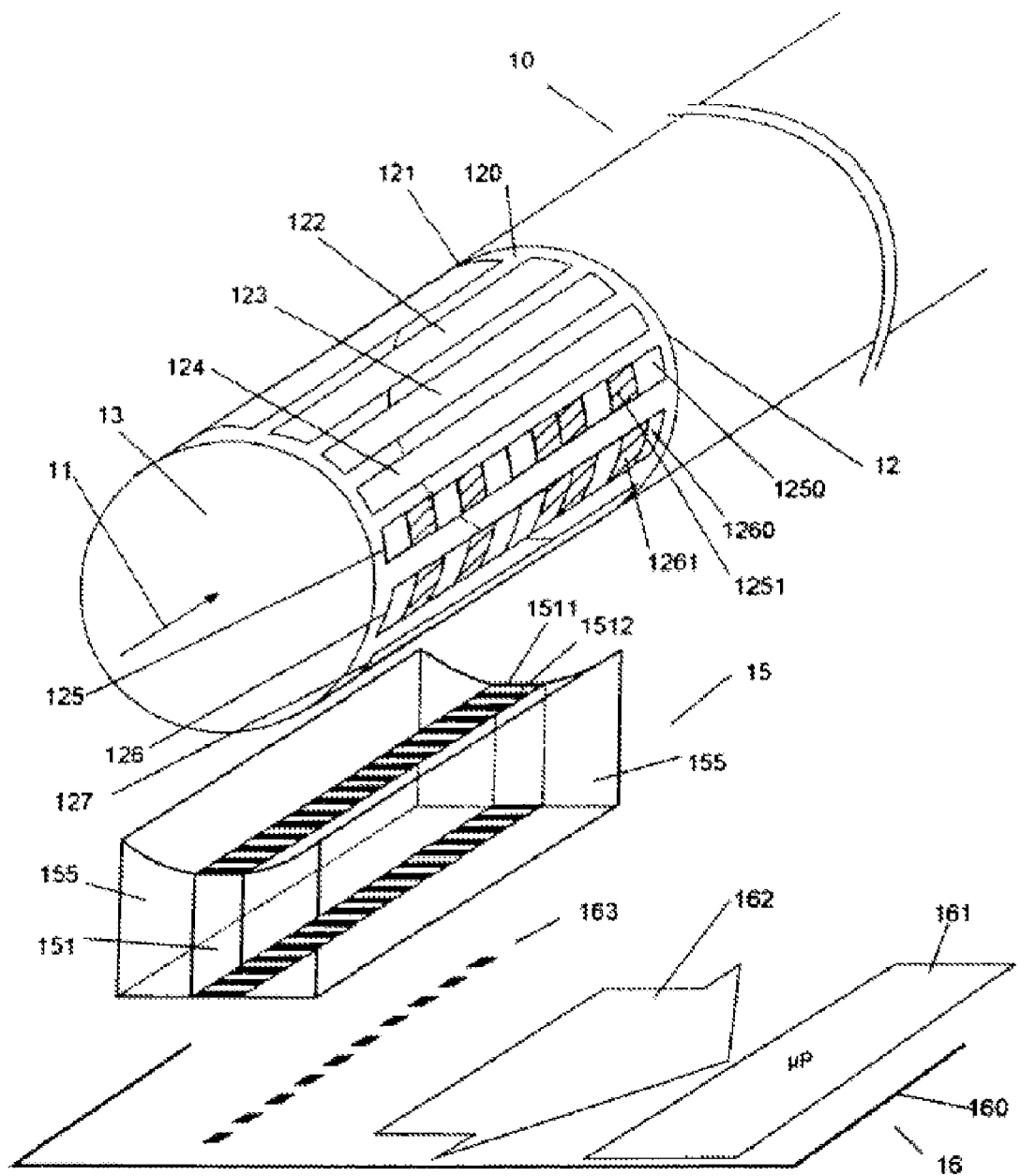
FIG. 1 shows a cartridge containing an electrically readable information in the form of patterns of patches in the axial direction of the cartridge and a support according to the invention comprising one electrically connecting support for transferring the information to an electronic circuit.
Figure 2:
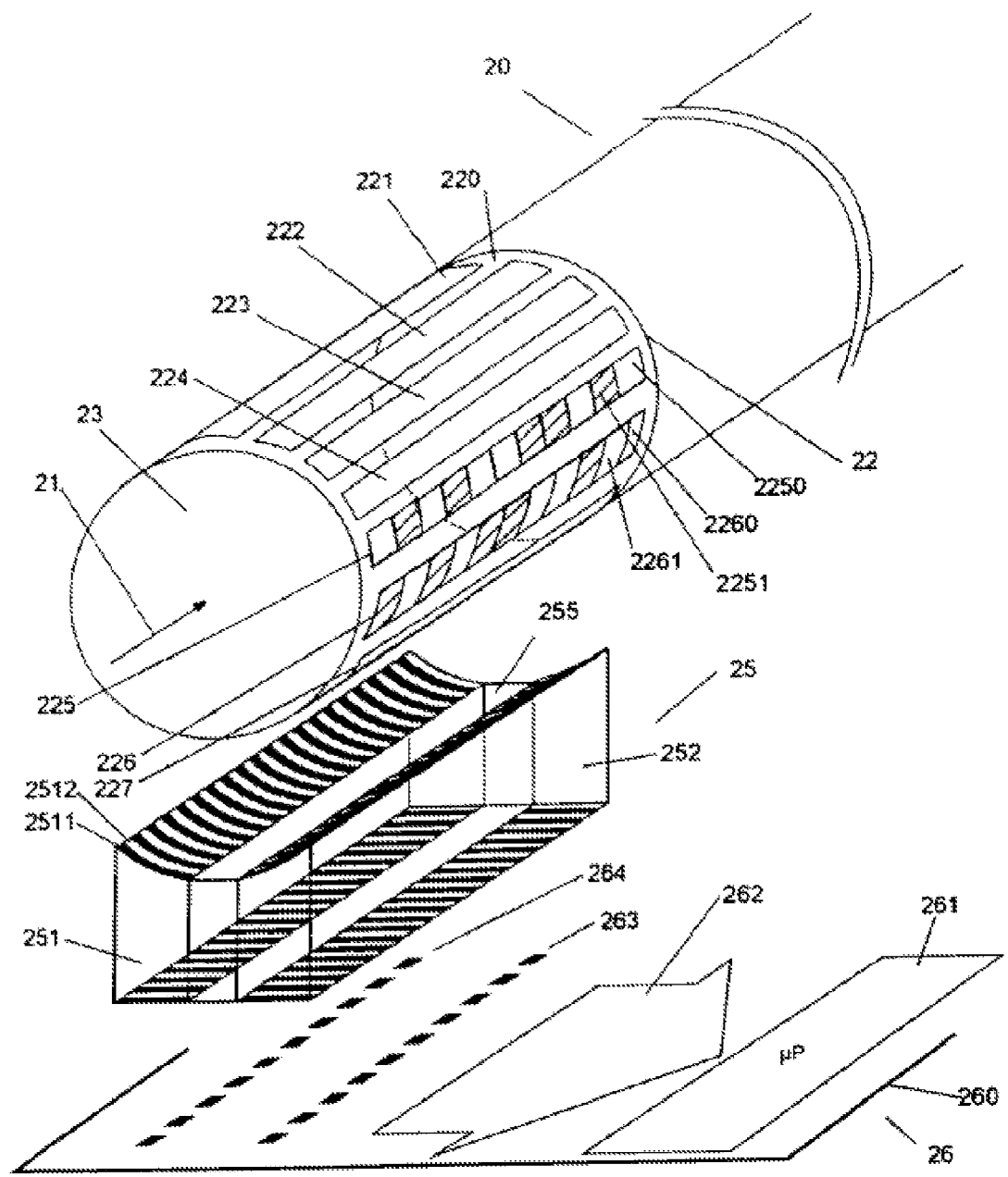
FIG. 2 shows a cartridge containing an electrically readable information in the form of patterns of patches in the axial direction of the cartridge and a support according to the invention comprising two electrically connecting supports for transferring the information to an electronic circuit.
Figure 3:
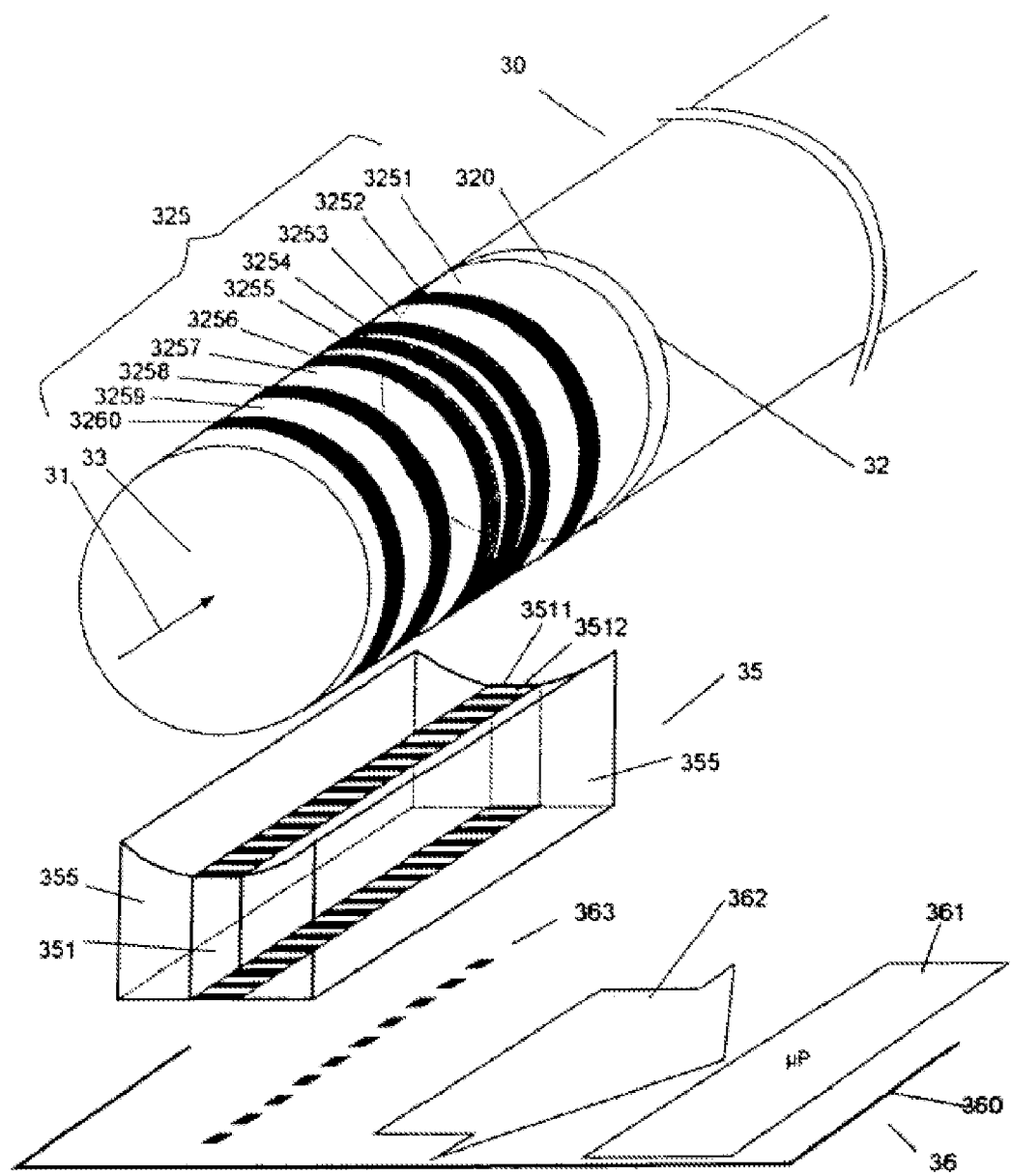
FIG. 3 shows a cartridge containing an electrically readable information in the form of ring patterns and a support according to the invention comprising one electrically connecting support for transferring the information to an electronic circuit, FIGS. 4.a-4.e show various ways of placing information carrying areas for holding electronically readable information on a cartridge, FIGS. 5.a-5.e show various ways of laying out the electrically conducting and electrically insulating areas in predefined positions within an information carrying area, implementing a binary representation of an item of information in its true and inverted form, FIGS. 6.a-6.c show various geometries of an electrically connecting support according to the invention, FIGS. 7.a and 7.b show an example of a cartridge and a support according to the invention comprising three electrically connecting supports made of elastic materials.

FIGS. 1-3 show a cartridge containing an electrically readable information in the form of patterns of electrically conducting and electrically insulating areas and a support according to the invention comprising one or more electrically connecting supports for transferring the information to an electronic circuit.

A support according to the invention has the combined function of receiving and mechanically supporting a part of the cartridge provided with information carrying areas AND of transferring the information from the these information carrying areas to an electronic circuit for further processing.

With reference to FIGS. 1, 2 and 3 (having reference numerals starting with 1, 2 and 3, respectively), the cartridge 10, 20, 30, respectively, is only partially shown, as indicated by the 'broken' outline in the right-hand part of the cartridge. The cartridge possesses a rotational symmetry as indicated by the arrow 11, 21, 31, symbolizing the axis of symmetry. A label 12, 22, 32 containing information carrying areas laid out in the axial direction of the cartridge, is located on the outer surface at one axial end of the cartridge, where a lid 13, 23, 33, optionally in the form of a piston when the cartridge is a replaceable medication cartridge for a medication delivery device, provides a closure of the cartridge.

The label 12, 22, 32 comprises an electrically conducting foil 120, 220, 320 having information carrying areas 121-127, 221-227, 325 extending in the axial direction of the cartridge. In FIGS. 1 and 2, a multitude of information carrying areas (121-127, 221-227, respectively, plus the ones situated on the hidden part of the surface) are evenly distributed on the surface of the cartridge in a radial direction (i.e. along the whole periphery encircling the axial direction of the cartridge). Each information carrying area, comprising patterns of electrically conducting and electrically insulating patches, thus only covers a limited radial sector of the surface. In FIG. 3, on the other hand, only one information carrying area 325 is indicated. This extends, however, along the whole periphery of the cartridge (i.e. the item of information is represented by closed rings 3251-3260 of electrically conducting and electrically insulating areas).

Each of the information carrying areas 121-127, 221-227, 325 contains an item of information in the form of patterns of electrically conducting and electrically insulating areas. Each pattern represents an item of information in binary form. Each bit of information is represented by an electrically characteristic layer in a predefined position in the information carrying area. A binary one in a specific predefined position may be represented by an electrically conducting layer covering that predefined position, and a binary zero in a specific predefined position may be represented by an electrically insulating layer covering that predefined position. Alternatively, binary one may be represented by an insulating layer and binary zero by a conducting layer.

Because the foils 120, 220, 320 in FIGS. 1-3 containing the information carrying areas 121-127, 221-227, 325 are electrically conducting, it is only necessary to apply an electrically insulating layer (e.g. a paint) to the predefined positions representing one of the a binary states (in this embodiment 'zero').

In FIGS. 1-3, the cartridge is shown in a position just above the support 15, 25, 35, respectively, which, again for illustrative purposes, is shown just above a PCB with electronic components and connecting wires 16, 26, 36 containing pads 163, 263, 264, 363 with electrical connections, symbolically indicated by an arrow 162, 262, 362, to a processing unit 161, 261, 361, e.g. a microprocessor. The support consists of one or more electrically connecting supports 151, 251, 252, 351 embedded in an electrically insulating material 155, 255, 355. The electrically connecting supports comprise alternating layers of electrically conducting 1511, 2511, 3511 and electrically insulating 1512, 2512, 3512 layers of an elastomeric material, e.g. silicone rubber with the electrically conducting layer having a concentration of carbon black sufficient for electrical conduction. Each electrically conducting layer is electrically insulated from all other electrically conducting layers, so that each electrically conducting layer in effect represents an insulated conductor. By controlling the layer thicknesses, the maximum 'density of information' in the axial direction may be controlled.

In the embodiments of FIGS. 1-3, the supports 15, 25, 35, including the electrically connecting supports 151, 251, 252, 351, are shown to be adapted to receive the curved shape of the part of the cartridge, where the information carrying areas 121-127, 221-227, 325 are located, by shaping them equivalently. This makes possible the use of non-elastic materials for the support, if convenient.

In an operating configuration, the support is placed (and optionally fastened) on the PCB 160, 260, 360 so that electrical contact between the electrically connecting supports 151, 251, 252, 351 and the pads 163, 263, 264, 363 is ensured. The cartridge is positioned on the support so that electrical contact between one (FIGS. 1, 3) or two (FIG. 2) of the information carrying areas in their full axial lengths (i.e. involving all patches of a given information carrying area representing bits of information) and the electrically connecting supports is ensured. The geometrical dimensions of the patches, layers and pads and mutual distance between adjacent information carrying areas on the cartridge and corresponding electrically connecting supports are discussed below with reference to FIGS. 6 and 8.

By applying a specific electric potential to the electrically conducting foil 120, 220, 320, this potential will be transferred from those predefined areas containing a conductive layer (i.e. in the present embodiment those predefined areas not being covered by an insulating layer) to the corresponding pads on the PCB. Via the connecting circuitry, a direct measure of the pattern of binary states of the information carrying area connected to the pads by a given electrically connecting support is presented on the inputs of the processing unit, possibly by appropriately terminating the inputs with pull-up or pull-down circuitry depending on the potential applied to the electrically conducting foil and the definition of the binary states. A specific part of the foil may be preferably reserved to the application of the electric potential (e.g. an area of the foil circumfering the cartridge and not occupied by information carrying areas, in FIG. 3 e.g. the part of the foil 320 not covered by information bits in predefined positions 321-330).

The support 15, 25, 35 is only shown as having an axial length corresponding to the axial length of the corresponding information carrying areas (e.g. 125 in FIG. 1) but it may of course extend in both axial directions if appropriate for the application in question. Likewise the support is shown to cover a certain radial sector (less than 90 degrees), but it may of course cover any radial sector, including 360 degrees, if appropriate. In a preferred embodiment, the sector covered by the support is less than 180 degrees allowing a direct 'vertical' placement of the cartridge in the support (in opposition to the case of a 360 degrees support, where the cartridge has to be axially inserted).

In FIGS. 1-3, the label 12, 22, 32 containing information carrying areas 121-127, 221-227, 325 is placed in one axial end of the cartridge 10, 20, 30 covering only the space occupied by the axial extent of the lid/piston 13, 23, 33 to ensure that a full view of the contents of the cartridge is available for inspection. Of course it might be located in any convenient position along the surface of the cartridge. Similarly, in FIGS. 1-3, the information carrying areas extend in the axial direction of the cartridge. They might as well extend in a radial direction (as discussed in connection with FIGS. 4 and 5) or in a direction there between (e.g. forming one or more helixes on the surface of the cartridge), if convenient, as long as the support, including the electrically connecting support(s), is adapted thereto.

The electrical connections, schematically indicated by an arrow 162, 262, 362, connecting the pads 163, 263, 264, 363 with the processing unit 161, 261, 361 may be a one to one parallel set of electrical connections between each pad and a corresponding input on the processor 161, 261, 361, but it may also comprise a multiplexing or coding unit to reduce the number of necessary inputs to the processing unit.

FIG. 1 shows a cartridge containing an electrically readable information in the form of patterns of patches in the axial direction of the cartridge and a support according to the invention comprising one electrically connecting support for transferring the information to an electronic circuit. The binary information contained in each of the information carrying areas 121, 122, 123, 124, 125, 126, 127 is the same as schematically indicated in the information carrying areas 125 and 126 in that the patterns of electrically conducting patches, exemplified by 1250, 1260 (no filling), and electrically insulating patches, exemplified by 1251, 1261 (hatched), are identical.

The embodiment in FIG. 1 benefits from the rotational symmetry of the cartridge 10 and the label 12 with identical information carrying areas 121-127 equally distributed on the label along the periphery of the cartridge in that it only requires the user to position the cartridge properly in a radial direction (possibly involving a slight rotation of the cartridge around its axis of symmetry) to ensure that an electrical contact between one of the information carrying areas 121-127 and the electrically connecting support 151 is present (since the positioning in an axial direction 11 may be mechanically ensured by receiving means for the cartridge). The control of the cartridge being correctly positioned may be in the hands of the processing unit 161, which, if necessary, may indicate to the user via a display (not shown) or a voice interface that a corrective action is required, and which may block further use of the device, if the cartridge is not correctly positioned.

FIG. 2 shows a cartridge containing an electrically readable information in the form of patterns of patches in the axial direction of the cartridge and a support according to the invention comprising two electrically connecting supports for transferring the information to an electronic circuit.

In the embodiment in FIG. 2, the support 25 comprises two electrically connecting supports 251, 252 for simultaneously reading two items of information from two information carrying areas (e.g. 225, 226) on the cartridge 20. In FIG. 2 the evenly distributed information carrying areas 221-227 contain an item of information in a true binary form alternating with the information in its inverted form as indicated by the schematically illustrated patterns of electrically conducting 2261 and insulating 2251 patches in information carrying areas 225 and 226, respectively, one pattern being the inverse of the other. Apart from the advantages of the rotational symmetry as described above in connection with FIG. 1, the embodiment of FIG. 2 has the advantage of reading the information in a binary true and inverted form, which allows the safety in reading to be improved. Instead of providing the information in its true and inverted forms, the same binary representation of the item of information may be provided in all information carrying areas (as in FIG. 1) and read twice, which also allows an improved safety in reading. In the embodiment of FIG. 2, the electrically conducting 'end'-patches 2250, 2260 may be used for connecting a power supply voltage.

FIG. 3 shows a cartridge containing an electrically readable information in the form of ring patterns and a support according to the invention comprising one electrically connecting support for transferring the information to an electronic circuit.

In the embodiment in FIG. 3, the support 35 comprises only one electrically connecting support 351 for reading an item of information from an information carrying area 325 on the cartridge 30. The information carrying area 325 extends along the whole periphery of the cartridge 30. A binary representation of the item of information is implemented by closed rings 3251-3260 of electrically conducting and electrically insulating areas in predefined positions. This embodiment has the advantage of having a full rotational symmetry so that the cartridge 30 may be (radially) arbitrarily oriented in the support.

FIGS. 4.*a*-4.*e* show various ways of placing information carrying areas for holding electronically readable information on a cartridge.

FIGS. 4.a-4.d show a cartridge 40 with an axis of rotational symmetry 41 and information carrying areas located at one axial end of the cartridge.

FIG. 4.a shows two information carrying areas 401, 402 positioned side by side in a radial direction on the surface of the cartridge 40 (i.e. along the periphery perpendicular to the axis of symmetry). Each information carrying area covers only a limited radial sector of the surface.

FIG. 4.b shows two information carrying areas 403, 404 positioned side by side in the axial direction 41 on the surface of the cartridge 40 (i.e. along the periphery parallel to the axis of symmetry). Each information carrying area 403, 404 covers only a limited radial sector of the surface.

FIG. 4.c shows two information carrying areas 405, 406 positioned side by side in the axial direction on the surface of the cartridge 40 (i.e. along the periphery parallel to the axis of symmetry 41). Each information carrying area 405, 406 encircles the entire radial periphery of the cartridge.

FIG. 4.d shows information carrying areas 410, 411, 412, 413, 414 positioned side by side, evenly distributed in a radial direction on the surface of the cartridge 40 (i.e. along the periphery perpendicular to the axis of symmetry). Each information carrying area covers only a limited radial sector of the surface. Information carrying areas 410, 411, 412, 413, 414 plus identical ones situated on the hidden part of the surface are evenly distributed on the surface of the cartridge in a radial direction, i.e. extending along the whole periphery encircling the axial direction of the cartridge.

FIG. 4.e shows an information carrying area 415 extending along the major part of the axial length of the cartridge 40. The information carrying area is located within in a surface area 420 corresponding to a radial sector 421. In FIG. 4.e a single information carrying area is shown within the surface area 420. There might as well, however, be several information carrying areas located side by side in axial (cf. FIG. 4.b) or radial (cf. FIG. 4.a) direction.

FIGS. 5.a-5.e show various ways of laying out the electrically conducting and electrically insulating areas in predefined positions within an information carrying area, implementing a binary representation of an item of information in its true and inverted form.

In each of FIGS. 5.a-5.e two information carrying areas containing an item of information in a true and inverted binary form, respectively, are schematically shown. Each information carrying area has a rectangular shape defining a longitudinal direction as the direction defined by its longest side. A direction is also defined by the direction perpendicular to the face between two neighboring predefined positions each containing a specific bit of information.

FIG. 5.a shows an embodiment with two information carrying areas 50, 51 located side by side in a direction perpendicular to the direction 505 defined by adjacent predefined positions. Each individual bit of information is implemented as a patch of electrically conducting 511 (no filling) or electrically insulating 501 (hatched) material located at a specific predefined position of the information carrying area. Neighboring patches abut each other. The structure of information carrying areas 50, 51 may e.g. be used in FIGS. 4.a. and 4.d.

FIG. 5.b shows an embodiment with two information carrying areas 52, 53 located side by side in a direction perpendicular to the direction 525 defined by adjacent predefined positions. Each individual bit of information is implemented as a patch of electrically conducting 531 (no filling) or electrically insulating 521 (hatched) material located at a specific predefined position of the information carrying area. Neighboring patches are separated by a an 'empty' space 520, 530 of width equal to the width of each of the information carrying patches 521, 531. The 'empty' space may consist of an electrically conducting or insulating layer (as long as the pads on the PCB (cf. FIGS. 1-3) are correspondingly laid out). The structure of information carrying areas 52, 53 may e.g. be used in FIGS. 4.a. and 4.d.

FIG. 5.c shows an embodiment with two information carrying areas 54, 55 located side by side in a direction 545 defined by adjacent predefined positions. Each individual bit of information is implemented as a patch of electrically conducting 551 (no filling) or electrically insulating 541 (hatched) material located at a specific predefined position of the information carrying area. Neighboring patches abut each other. The structure of information carrying areas 54, 55 may e.g. be used in FIGS. 4.a. and 4.d.

FIG. 5.d shows an embodiment with two information carrying areas 56, 57 located side by side in a direction 565 defined by adjacent predefined positions. Each individual bit of information is implemented as a patch of electrically conducting 562, 571 (no filling) or electrically insulating 561, 572 (hatched) material located at a specific predefined position of the information carrying area. Neighboring patches abut each other. The structure of information carrying areas 56, 57 may e.g. be used in FIGS. 4.b. and 4.c.

FIG. 5.e shows an embodiment with two information carrying areas 58, 59 located side by side in a direction perpendicular to the direction 585 defined by adjacent predefined positions. Each individual bit of information is implemented as a patch of electrically conducting 591 (no filling) or electrically insulating 581 (hatched) material located at a specific predefined position of the information carrying area. Neighboring patches abut each other. The structure of information carrying areas 58, 59 may e.g. be used in FIGS. 4.b. and 4.c.

FIGS. 6.a-6.c show various geometries of an electrically connecting support according to the invention.

Common for FIGS. 6.a-6.c is that the layer thicknesses 630, 640 of the electrically insulating and conducting layers, respectively, are exaggerated compared to the dimensions of the patches 61 on the information carrying areas and the pads 62 on the PCB.

FIG. 6.a shows an embodiment of an electrically connecting support 60, where the thickness $T_{il}$ 630 of the insulating layer 63 is larger than the thickness $T_{cl}$ 640 of the conducting layer 64. The patches 61 of the information carrying area are shown to be of equal width Wpda 610 and to abut each other. The pads 62 on the PCB are shown to have equal width Wcp 620 and to be evenly distributed with a distance Diacp 621 between each pad.

FIG. 6.b shows an embodiment of an electrically connecting support 60, where the thickness $T_{il}$ of the insulating layer 63 is smaller than the thickness $T_{cl}$ of the conducting layer 64.

FIG. 6.c shows an embodiment of an electrically connecting support 60, where the thickness $T_{il}$ of the insulating layer 63 equals the thickness $T_{cl}$ of the conducting layer 64.

The relation Diacp>2*$T_{cl}$ makes sure that the electrical states of adjacent information carrying patches on the cartridge are not transferred to the same pad in the contact area under the assumption that the border between adjacent patches is located at a position 'corresponding to midway between two pads'. The fulfillment of the relation Wcp>$T_{il}$+$T_{cl}$ ensures that at least one conducting layer contacts any given pad. Correspondingly, the fulfillment of the relation Wpda>$T_{il}$+$T_{cl}$ ensures that each patch has contact to at least one of the conducting layers of an electrically connecting support, when the cartridge is properly placed in the support.

In FIGS. 6.a-6.c, the information carrying patches on the cartridge are shown as abutted. This need not be the case. They may have any width Wpda as long as the relation Wpda>$T_{il}$+$T_{cl}$ is fulfilled to ensure that at least one conducting layer contacts any given information carrying patch.

The relations reflect the minimum distances of pads and patches and between pads and thus for given layer thicknesses determine the information density (minimum width per bit).

FIG. 7.a-7.b show an example of a cartridge and a support according to the invention comprising three electrically connecting supports made of elastic materials.

FIG. 7.a shows a cartridge 71 having an axis of rotational symmetry 72 being positioned just above a support 70 comprising three individual electrically connecting supports 701, 702, 703 ready for receiving the cartridge. The cartridge is provided with information carrying areas positioned on the cartridge along its radial periphery with a spacing corresponding to the geometry of the electrically connecting supports 701, 702, 703. The space between the electrically connecting supports may be filled with an isolating material (e.g. silicone rubber), not shown.

In FIG. 7.b the cartridge 71 is positioned in the support 70 and fixed with a slight downwards pressure indicated by the arrow 73. The support including the electrically connecting supports 701, 702, 703 is made of elastic materials so that it conforms to the shape of the cartridge over the axial length of the support, when the cartridge is placed in the support.

The three items of information that may be simultaneously read may be identical, in which case the redundancy may be used to improve the safety in reading (by a simple majority test or by more advanced error correcting techniques), or they may be different, in which case a larger amount of information may be read from the cartridge.

Figure 8:
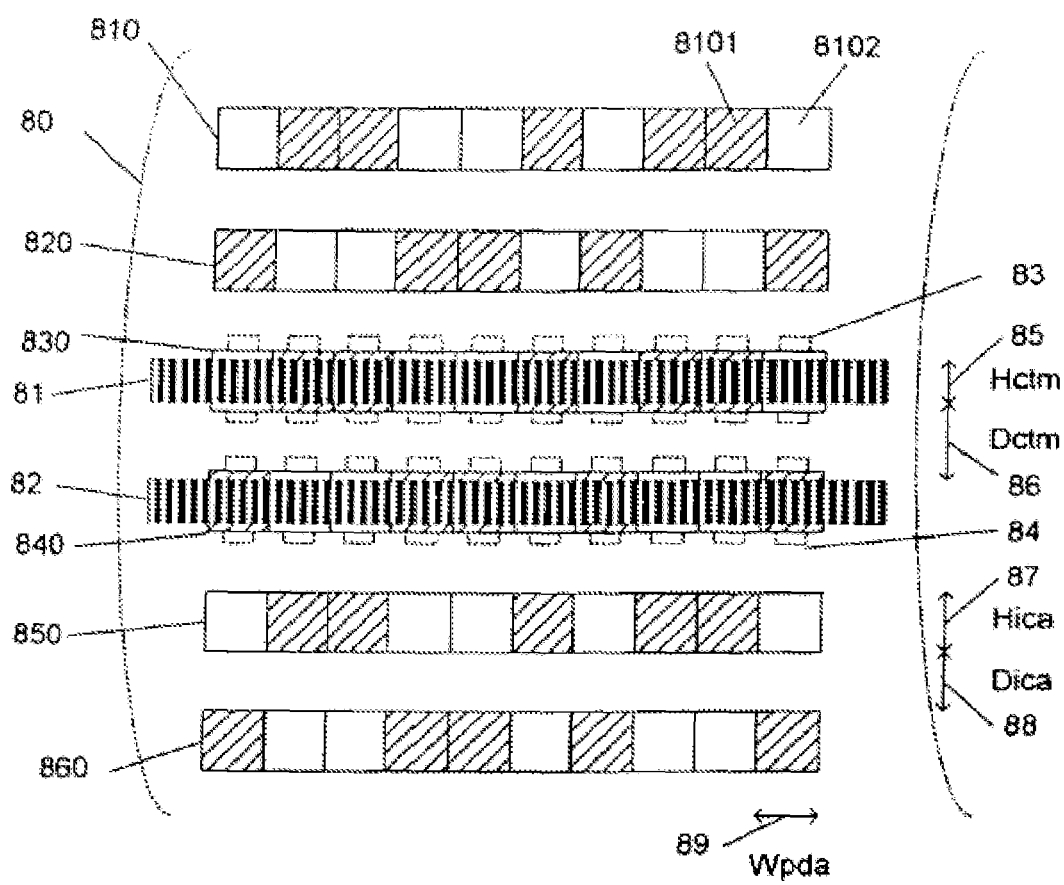
FIG. 8 shows geometries involved in reading an item of information provided a multitude of times along the periphery of a cartridge with a rotational symmetry by means of two electrically connecting supports.

FIG. 8 shows geometries involved in reading an item of information provided a multitude of times along the periphery of a cartridge with a rotational symmetry by means of two electrically connecting supports.

In FIG. 8, the electrically connecting supports 81, 82 are shown in a position where they read information from information carrying areas 830, 840, respectively, and transfer the information to groups of pads 83, 84, respectively, on a PCB. The information carrying areas 810, 820, 830, 840, 850, 860 on a label 80 carry an item of information alternatingly in a binary true and inverted form as indicated by the schematically shown individual patches of equal width Wpda 89. The patches are either electrically conducting 8102 (no filling) or electrically insulating 8101 (hatched).

The following geometric relations between the information carrying areas positioned on a cartridge and the electrically connecting supports 81, 82 of a support according to the invention for the cartridge:

*Hica<Dctm<2\*Hica+Dica*, and

*Hctm<Dica<2\*Hctm+Dctm*, where

Hica=Height 87 of information carrying areas
Dica=Distance 88 between information carrying areas
Hctm=Height 85 of electrically connecting supports
Dctm=Distance 86 between electrically connecting supports.

Hica<Dctm ensures that the cartridge cannot be positioned in such a way that a given information carrying area has contact to two electrically connecting supports at the same time.

Hctm<Dica ensures that the cartridge cannot be positioned in such a way that a given electrically connecting support has contact to two information carrying areas at the same time.

Dica<2*Hctm+Dctm ensures that the cartridge cannot be positioned in such a way that the electrically connecting supports fall entirely between two information carrying areas, in which case they would not have contact to any of the information carrying areas of the cartridge.

Dctm<2*Hica+Dica ensures that the cartridge cannot be positioned in such a way that two adjacent information carrying areas fall entirely between the electrically connecting supports, in which case the latter might not have contact to any of the information carrying areas of the cartridge.

In a preferred embodiment, the following relation is fulfilled (in addition to the above mentioned relations between Dctm, Hctm, Dica, Hica), Dctm+Hctm=Dica+Hica, which ensures that the electrically connecting supports 81, 82 will have contact to two of the information carrying areas irrespective of the radial orientation of the cartridge in the support.

Some preferred embodiments have been shown in the foregoing, but it should be stressed that the invention is not limited to these, but may be embodied in other ways within the subject-matter defined in the following claims. The invention may for example be applied to the electronic marking of cartridges for other purposes than medical, e.g. film cartridges, various cassettes containing media holding digital data or analog signals (e.g. representing software, data, film or music), etc., that are used in an electronic 'environment' (e.g. in a camera, computer, recorder, player, viewer, etc.).

I claim:

1. A support for a medication holding cartridge provided with one or more electronically readable items of information carrying area, wherein the support is at least partially made from one or more electrically connecting supports, each comprising a plurality of closely spaced mutually electrically insulated conductors having a conducting layer thickness $T_{cl}$, and embedded in an electrically insulating material having an insulating layer thickness $T_{il}$ that stretches from one of the supporting surfaces of the cartridge to a contact area for receiving and transferring the information when the cartridge is positioned in the support and wherein the cartridge has an axis of symmetry and the contact area comprises a group of regularly spaced electrically conducting pads of width $W_{cp}$, with adjacent electrically conducting pads being separated by an electrically insulating area a distance $D_{iacp}$ and wherein $D_{iacp}>(2*T_{cl})$.

2. The support of claim 1, wherein $W_{cp}>T_{il}+T_{cl}$.

* * * * *